US005777166A

United States Patent [19]
Cordier et al.

[11] Patent Number: 5,777,166
[45] Date of Patent: Jul. 7, 1998

[54] PROCESS FOR THE CATALYTIC HYDROGENATION OF NITRILES TO AMINES IN THE PRESENCE OF A CATALYST OF DOPED RANEY NICKEL TYPE

[75] Inventors: Georges Cordier, Francheville; Pierre Fouilloux, Caluire-et-Cuire; Nathalie Laurain; Jean-Francis Spindler, both of Lyons, all of France

[73] Assignee: Rhone-Poulenc Chimie, Courbevoie Cedex, France

[21] Appl. No.: 663,097

[22] PCT Filed: Dec. 16, 1994

[86] PCT No.: PCT/FR94/01478

§ 371 Date: Nov. 25, 1996

§ 102(e) Date: Nov. 25, 1996

[87] PCT Pub. No.: WO95/18090

PCT Pub. Date: Jul. 6, 1995

[30] Foreign Application Priority Data

Dec. 28, 1993 [FR] France ................... 93 16008

[51] Int. Cl.[6] ................ C07C 209/00; B01J 25/00
[52] U.S. Cl. ........................... 564/491; 502/301
[58] Field of Search .................... 564/385, 491; 502/301

[56] References Cited

U.S. PATENT DOCUMENTS 3,862,911  1/1975  Chabert ................... 252/470

4,248,799  2/1981  Drake ..................... 564/491

OTHER PUBLICATIONS

Russian Chemical Reviews, Uspekhi Khimii, vol. 33, 1964.

Chemical Abstracts, vol. 92, No. 22, Jun. 2, 1980, Abst. #92:182869v.

Primary Examiner—José G. Dees
Assistant Examiner—Alton Pryor
Attorney, Agent, or Firm—Burns, Doane, Swecker & Mathis, L.L.P.

[57] ABSTRACT

The present invention relates to the field of the catalytic reduction of nitriles to amines by use of Raney catalysts doped with one or a number of additional metal elements chosen from the elements of group IVb of the periodic classification.

More precisely, it relates to a process for the hydrogenation of nitriles to amines, characterized in that it essentially consists:

in selecting a liquid reaction medium which dissolves the nitrile substrate to be hydrogenated, in using at least one inorganic alkali metal or alkaline-earth metal hydroxide base, and in adopting a catalyst whose doping element/Ni ratio by weight is between 0.05 and 10%.

More specific application to the hydrogenation of dinitriles to diamines or to aminonitriles.

25 Claims, No Drawings

PROCESS FOR THE CATALYTIC HYDROGENATION OF NITRILES TO AMINES IN THE PRESENCE OF A CATALYST OF DOPED RANEY NICKEL TYPE

This application is a 371 of PCT/FR94/01478 Dec. 16, 1994.

The present invention relates to the huge field of the catalytic reduction of nitriles, in particular of mononitriles and/or dinitriles, to monoamines, diamines or aminonitriles by use of Raney catalysts doped with one or a number of additional metal elements.

More precisely, the subject of the present invention is a process for the hydrogenation of nitriles to amines, for example of mononitriles and/or dinitriles to monoamines and/or diamines, using a catalyst of Raney nickel type doped with at least one additional metal element chosen from group IVb of the periodic classification and resulting from an Ni/Al/doping element(s) metallurgic precursor alloy.

The reduction of nitriles to amines, for example of dinitriles to diamines, is a chemical conversion which assumes the greatest importance in the chemical industry because amines, and in particular diamines, are compounds which are often used as reactive monomers in polycondensation reactions, for example with other bifunctional monomers. A particularly illustrative example of this large-scale industrial dimension is that of adiponitrile, which is capable of being hydrogenated to hexamethylenediamine. This last compound is one of the basic monomers in the manufacture of polyamide-6,6, the economic importance of which is known.

This reduction of nitriles to amines must also be understood as comprising the conversion of dinitriles to aminonitriles, for example of adiponitrile to aminocapronitrile, it being possible for the latter to be converted to caprolactam by cyclizing hydrolysis. Caprolactam itself is also a fundamental compound in the chemistry of polymer fibers, since it constitutes the monomer of polyamide-6.

The hydrogenation of nitriles to amines is conventionally carried out with the catalytic support of, optionally doped, Raney nickel. These catalysts are prepared by leaching the aluminium from aluminium-rich Al/Ni alloys, in strongly alkaline medium. The catalysts obtained consist of agglomerates of nickel crystallites having a high specific surface and a variable residual aluminium content.

Modification of the structural and electronic factors of Raney nickel, by addition of metals to the nickel/aluminium alloy, has already been envisaged. The addition of a doping agent is conventionally carried out by introduction into an Ni/Al precursor alloy in the molten state. It relates to metallurgic doping. Thus, the doping of Raney nickel with various metal promoters (Fe, Co, Cr, Mn, V, Mo, Zr, Ta or Ti), as well as their effects as regards the activity, selectivity and stability of the catalyst, form the subject of a rich scientific and techical literature.

The article by Freidlin et al. (*Russian Chemical Review*, Vol. 33, No. 6, June 1964) relates to the catalytic reduction of dinitriles and lists a certain number of doped Raney catalysts used under varied hydrogenation conditions (temperature, hydrogen pressure ($P_{H_2}$), reaction medium). Mention is particularly made of Raney nickels doped with chromium, copper and titanium. With Raney Ni doped with chromium, the hydrogenation is carried out in acetic anhydride in the presence of NaOH at a temperature of 50° C. and a hydrogen pressure of approximately 0.35 MPa to obtain a selectivity of 77% for diamine from adiponitrile. As regards Raney Ni doped with titanium, the reaction medium contains butanol and ammonia, the temperature is from 140° C. to 180° C., the hydrogen pressure approximately 14 MPa and the selectivity for diamine is 60% from dicyanobenzene. It also appears that the doping elements (such as Ti) are present in an amount greater than or equal to 4% by weight with respect to the nickel.

It is observed that the selectivities obtained in the hydrogenations of dinitriles using doped Raney Ni described in this prior document are relatively low. In addition, in certain cases, the reaction conditions, such as the temperature and the hydrogen pressure, are at such high levels that they are harmful to the convenience of implementation of the process and to its economics.

Patent FR-A 2,068,963 relates to Raney Ni catalysts doped with chromium by the metallurgic route.

A first disadvantage of the use of chromium as doping agent is due to the fact that this metal is capable, in certain cases, of being regarded as being able to cause problems as regards pollution.

A second disadvantage is that chromium does not make it possible to achieve negligible contents of nitrile hydrogenation impurities such as, for example, diaminocyclohexane (DCH). These impurities are a particular nuisance because they have substantially the same boiling temperature as the targeted amines and are thus very difficult to remove.

There therefore exists a certain industrial need for the optimization of the conditions for the hydrogenation of nitriles to amines, especially of dinitriles to aminonitriles and/or diamines, by means of catalysts of doped Raney Ni type, especially with respect to the operating conditions as well as the activity, selectivity and stability of the final catalyst.

Such an optimization constitutes one of the essential subjects of the present invention, which comprises a process for the hydrogenation of nitriles to amines which is easy to implement, non-polluting and economic and which makes it possible, on the one hand, to achieve selectivities for diamine which are greater than 90%, expressed with respect to the starting nitrile substrate, and, on the other hand, to reduce the impurities as far as possible.

It therefore relates more precisely to a process for the hydrogenation of nitriles to amines using a catalyst of Raney Ni type, characterized in that:

the said catalyst is doped with at least one additional metal element chosen from group IVb of the periodic classification and resulting from an Ni/Al/doping element(s) metallurgic precursor alloy, and in that the said process consists essentially:

in selecting a liquid reaction medium which dissolves the nitrile substrate to be hydrogenated, in using at least one inorganic base chosen from alkali metal or alkaline-earth metal hydroxides and in adopting a catalyst whose doping element/Ni ratio by weight is between 0.05 and 10%.

It is to the credit of the Applicant company to have developed an outstanding hydrogenation process resulting from a technical compromise between, on the one hand, a Raney Ni catalyst doped with specific amounts of additional elements and, on the other hand, carefully chosen reaction conditions.

Thus, the doped Raney Ni catalyst used in this process arises from a molten Ni/Al precursor alloy (Ni content of 28 to 59% weight for weight) to which at least one additional metal element, preferably titanium, is added, according to a so-called "metallurgic" doping procedure. After cooling, the doped precursor alloy is conventionally subjected to an alkaline attack causing more or less significant removal of the aluminium and, optionally, of a fraction of the doping element.

The starting alloys used are chosen from the following forms of binary nickel/aluminium combinations: $NiAl_3$, $Ni_2Al_3$ and $Al/NiAl_3$ proeutectic.

In accordance with the invention, it is advantageous to choose the doping agent(s) from the metals of group IVb of the transition elements. Titanium has proved to be particularly appropriate as an additional element of Raney Ni. On the quantitative level, the doping agent is preferably overdosed in the precursor alloy before alkaline attack, so as to take into account its removal.

In practice, a Ti/Ni ratio by weight varying from 0.6 to 4.5% for the finished catalyst is preferred.

This process applies, more particularly but non-limitingly, to the nitrile substrates of formula (I):

NC—R—CN      (I)

in which R represents a linear or branched alkylene or alkenylene group having from 1 to 12 carbon atoms or a substituted or unsubstituted arylene or aralkylene or aralkenylene group.

Use is preferably made in the process of the invention of dinitriles of formula (I) in which R represents a linear or branched alkylene radical having from 2 to 6 carbon atoms.

Mention may be made, as examples of such dinitriles, of especially adiponitrile, methylglutaronitrile, ethylsuccinonitrile, malononitrile, succinonitrile and glutaronitrile and their mixtures, especially adiponitrile, methylglutaronitrile and ethylsuccinonitrile mixtures which arise from the same process for the synthesis of adiponitrile.

Introduction of the nitrile substrate, for example adiponitrile, into the reaction medium is carried out while observing a concentration of between 0.001% and 30% by weight with respect to the total weight (w/w) of the reaction medium and preferably between 0.1% and 20% w/w.

The strong base used is preferably chosen from the following compounds: LiOH, NaOH, KOH, RbOH, CsOH and their mixtures.

In practice, use is preferentially made of NaOH and KOH, for a good compromise between performance and price, although RbOH and CsOH give even better results.

The hydrogenation reaction medium is preferably liquid. It contains at least one solvent capable of dissolving the nitrile substrate to be hydrogenated, it being known that this conversion takes place more readily when the said substrate is in solution.

According to an advantageous embodiment of the process according to the invention, use is made of an at least partially aqueous liquid reaction medium. Water is generally present in an amount less than or equal to 50%, advantageously less than or equal to 20%, by weight with respect to the total reaction medium. More preferentially still, the water content of the reaction medium is between 0.1 and 15% by weight with respect to all the constituents of the said medium.

To complement or substitute for the water, it is possible to provide at least one other solvent, of alcohol and/or amide type. Alcohols which are more particularly suitable are, for example, methanol, ethanol, propanol, isopropanol, butanol, glycols, such as ethylene and/or propylene glycol, polyols and/or mixtures of the said compounds.

In the case where the solvent consists of an amide, it can be, for example, dimethylformamide or dimethylacetamide.

When it is used with water, the solvent, which is preferably alcoholic, represents from two to four parts by weight per one part by weight of water and preferably three parts per one part of water.

According to another preferred characteristic of the invention, the amine whose preparation is targeted by the process is incorporated in the reaction medium. It is, for example, hexamethylenediamine when the nitrile substrate is adiponitrile.

The concentration of the targeted amine in the reaction medium is advantageously between 50% and 99% by weight with respect to all the solvent included in the said reaction medium and, more preferentially still, is between 60% and 99% by weight.

The amount of base in the reaction medium varies according to the nature of the reaction medium.

When the reaction medium contains only water and the targeted amine as liquid solvent medium, the amount of base is advantageously greater than or equal to 0.1 mol/kg of catalyst, preferably between 0.1 and 2 mol/kg of catalyst and more preferentially still between 0.5 and 1.5 mol/kg of catalyst.

In the case where the reaction medium comprises water and an alcohol and/or an amide, the amount of base is greater than or equal to 0.05 mol/kg of catalyst, is preferably between 0.1 and 10.0 mol/kg and more preferentially still between 1.0 and 8.0 mol/kg.

Once the composition of the reaction medium and the choice of the catalyst have been decided on, these two components are mixed and this mixture is then heated at a reaction temperature less than or equal to 150° C., preferably less than or equal to 120° C. and, more preferentially still less than or equal to 100° C.

In concrete terms, this temperature is between room temperature (approximately 20° C.) and 100° C.

Prior to, simultaneously with or subsequent to the heating the reaction chamber is brought to the appropriate hydrogen pressure, that is to say, in practice, between 0.10 and 10 MPa.

The duration of the reaction is variable according to the reaction conditions and the catalyst.

In a non-continuous operating mode, it can vary from a few minutes to a number of hours.

In a continuous operating mode, which it is entirely possible to envisage for the process according to the invention, the duration is obviously not a parameter which can be set.

It should be noted that a person skilled in the art can adjust the chronology of the stages of the process according to the invention, according to the operating conditions. The order given above only corresponds to a preferred, but non limiting, form of the process according to the invention.

The other conditions which govern the hydrogenation (in continuous or non-continuous mode) in accordance with the invention involve technical arrangements which are conventional and known in themselves.

By virtue of all the advantageous arrangements mentioned above, the process of the invention makes it possible to hydrogenate nitrile substrates to amines in a selective, fast convenient and economical way.

This process is perfectly suited for converting adiponitril to hexamethylenediamine, which is the precursor o polyamide-6,6, or to aminocapronitrile, which is the precursor of polyamide-6.

The invention will be better understood and its advantage and its implementational variants will clearly emerge from the examples which follow which illustrate, in a non limiting way, the hydrogenation process according to the invention, including the preparation of the catalyst.

EXAMPLES

General Protocol for the Preparation of the Raney Ni Hydrogenation Catalyst Doped with Titanium 1. Metallurgic Doping Various Ni/Al precursor alloy solid phases are available, namely: $NiAl_3$, $Ni_2Al_3$, NiAl, $Ni_3Al$, Al/NiAl$_3$ proeutectic, Al/NiAl$_3$ eutectic and their mixtures.

In these examples, the following are tested:

the proeutectic alloy with a Ni/Al ratio by weight of (28-x)/72, containing x % weight for weight of Ti, as-cast, the $NiAl_3$ alloy having an Ni/Al ratio by weight of (42-x)/58 and containing x % weight for weight of Ti, annealed for 48 h at 835° C., the $Ni_2Al_3$ alloy having an Ni/Al ratio by weight of (58-x)/42 and containing x % weight for weight of Ti, annealed for 48 h at 940° C.

The titanium employed arises from rods with a purity>99.9%.

Different Ti/Ni ratios by weight in the starting alloy are used: 1%, 2%, 3% and 4%.

Each alloy is brought to a melting temperature which is specific to it.

2. Alkaline Attack 300 ml of 6N sodium hydroxide solution are introduced into a 2 l, Teflon® round-bottomed flask at room temperature.

10.00 g of the above alloys are, moreover, weighed.

The alloy is introduced, using a spatula, into the sodium hydroxide solution at the rate of 20 g/h, so that the average temperature of the medium does not exceed 50° C.

When all the alloy has been added, there is a wait until effervescence has finished. After refluxing for 2 h, the supernatant solution is removed by separation by settling of the solid. The catalyst is washed with a boiling 1N sodium hydroxide solution and it is then replaced in a boiling 6N sodium hydroxide solution. After refluxing for 2 h, the catalyst is washed with boiling sodium hydroxide solutions of decreasing 6N, 3N, 2N and 1N concentrations.

The solid is recovered in a flank and stored in cold 1N sodium hydroxide solution.

Examples 1 to 7 and Comparative Tests A and B
Non-Continuous mode Hydrogenation: Catalytic Test 1. Equipment:

The reactor is a 150 ml autoclave made of 316 L stainless steel. It is equipped with a magnetic stirrer system (1500 rev/min, magnetic bar and counterblades) providing good gas/liquid transfer. Heating is carried out by means of a thermoregulated heating sleeve. The substrate to be hydrogenated is introduced via a steel dropping funnel surmounting the autoclave. It can also be introduced using a high-pressure pump in the case of a semi-continuous reactor. The hydrogen is stored under 5 MPa in a store equipped with a manometer connected to a recorder. It is pressure-released into the assembly at the constant pressure of the reaction. The kinetics of the reaction are monitored by recording the fall in pressure in the hydrogen store. Hydrogenate samples intended for analysis are withdrawn via a dip pipe equipped with a steel filter.

2. Products Used:

99.9% Adiponitrile (Rhône-Poulenc, M.W.=108.15).

99.9% Hexamethylenediamine (Rhône-Poulenc, M.W.= 116.21).

99.995% U Hydrogen by volume.

99.8% Ethanol.

Distilled water.

98% Sodium hydroxide, 86% potassium hydroxide.

Catalyst: Ti-doped Raney nickel described above.

3. Progression of a Non-Continuous-Type Test 3.1. Charges:

Adiponitrile (ADN): 6.0 g (0.055 mol).

Hydrogen: excess (>0.222 mol).

Reaction medium: hexamethylenediamine (HMD), $H_2O$ and generally EtOH forming the reaction solvent+ NaOH or KOH alkaline base: 42.0 g (0.10% of NaOH or KOH in the reaction medium), Catalyst: 0.40 g.

3.2. Procedure

An excess of Raney nickel slurry (1–2 g) is withdrawn and the catalyst is washed with six times 50 ml of distilled water. 0.40 g of catalyst is weighed exactly with a pycnometer. The wet Raney nickel is then introduced into the autoclave. For a catalyst mass of 0.40 g, the amount of water commonly entrained is of the order of 0.4 g. This water mass will be taken into account in the composition of the reaction solvent which must be 60/30/10 in HMD/ethanol/water (Examples 1 to 6 and Comparative Tests A and B) or 98/2 in HMD/water (Example 7). The alkaline base is introduced with the amount of water necessary for adjusting the required water percentages. All the handlings must take place under an argon atmosphere in order to minimize carbonation of the solvent and oxidation of the catalyst.

The autoclave is then purged with nitrogen and with hydrogen. The reactor is then heated to 80° C. and maintained under 2.5 MPa of hydrogen. Recording of the pressure in the hydrogen store is begun and the ADN is rapidly added. When hydrogen consumption becomes zero, the reactor is left stirring for a further half-hour in order for the end of the reaction to be better assessed.

At the end of the test, a hydrogenate sample is withdrawn in order to determine the selectivity. The initial activity and a "mean activity" are deduced from the curve of hydrogen consumption as a function of time.

3.3. Measurement of the Activity

The slope at the beginning of the hydrogen consumption curve is proportional to the initial rate (Ri), which has a kinetic meaning. This size is calculated by drawing up the quotient at the beginning of the number of moles of hydrogen consumed per unit of time corrected for the catalyst mass unit. The initial rate will be expressed in kmol of hydrogen consumed per kg of catalyst and per second.

In order for the performance of a catalyst to be well assessed, it is necessary to know if the initial activity is not burdened by premature ageing. This is why the mean reaction rate (Rm), which is the quotient of the number of moles of hydrogen brought into play to the total time of the reaction per catalyst mass unit and per second, is also measured.

The reproducibility of the test for the determination of Ri and Rm gives an uncertainty of less than 10%.

3.4. Measurement of the Selectivity (s)

At the end of the reaction, a hydrogenate sample is withdrawn and diluted approximately 40 times in isopropanol. This sample is quantitatively analysed by gas phase chromatography (GPC) using a semi-capillary column. The detector is a flame ionization detector. Quantitative determination of the by-products of the hydrogenation reaction of ADN is carried out by the internal standard method (undecane).

The list of the main by-products quantitatively determined is given below:

HMI: Hexamethyleneimine
AMCPA: Aminomethylcyclopentylamine
AZCHe: Azacycloheptene
NEtHMD: N-Ethylhexamethylenediamine
DCH: cis- and trans-Diaminocyclohexane
BHT: Bishexamethylenetriamine.

The selectivity (S) for HMD as a percentage is given by the relationship: 100-sum of the selectivities of the by-products. In fact, as HMD is used in the reaction solvent, it cannot be directly quantitatively determined very precisely. On the other hand, it has been verified that the by-products, taken as a whole, are all identified.

The selectivities for each of the by-products are represented by the molar percentage of the by-product formed with respect to the converted ADN. In all the examples and comparative tests carried out, the degree of conversion of the ADN (as well as that of the intermediate aminocapronitrile) is 100%.

The level of unsaturated products present in the hydrogenate can be evaluated by polarography.

3.5. Results of the Examples and Comparative Tests

Examples 1 to 6 and Comparative Tests A and B

HMD (60)/EtOH (30)/H$_2$O (10)+NaOH in a proportion of 0.10% by weight with respect to the weight of HMD/EtOH/H$_2$O The catalytic performances of Raney nickels doped with chromium (Comparative Tests A and B) were evaluated under the same pressure, temperature and reaction medium conditions as in Tests 2 and 6.

The catalyst of Test A is obtained from an NiAl$_3$ alloy. Its Cr/Ni ratio by weight is 0.6%.

The catalyst of Test B is obtained from an Ni$_2$Al$_3$ alloy. Its Cr/Ni ratio by weight is 3.5%.

Example 7

HMD (98) /H$_2$O (2)+KOH at 0.01% with respect to HMD/H$_2$O.

The results obtained are shown in Table 1 below.

TABLE 1

| Tests | Ni/Al Alloy % w/w | Doping agent % by wgt/Ni | Ri | Rm | S % for HMD | S % for DCH |
|---|---|---|---|---|---|---|
| Ex 1 | 26/72 | 1.4% Ti | 111 | 50 | 97.2 | 0.024 |
| Ex 2 | 40/58 | 1.2% Ti | 89 | 46 | 96.8 | 0.028 |
| Ex 3 | 57/42 | 0.73% Ti | 49 | 20 | 96.4 | 0.054 |
| Ex 4 | 56/42 | 1.33% Ti | 37 | 12 | 96.6 | 0.036 |
| Ex 5 | 55/42 | 2.48% Ti | 44 | 17 | 95.8 | 0.039 |
| Ex 6 | 54/42 | 3.48% Ti | 37 | 15 | 96.2 | 0.039 |
| Tc A | 43/58 | 0.6% Cr | 37 | 16 | 97.1 | 0.044 |
| Tc B | 54/42 | 3.5% Cr | 145 | 55 | 96.8 | 0.065 |
| Ex 7 | 55/42 | 2.48% Ti | 21 | 4 | 95.6 | 0.037 |

It is noted that the DCH impurities (cis+trans) are present in very small amounts. This constitutes a significant advantage which counts in favour of the invention because these impurities have virtually the same boiling temperature as HMD and are therefore very difficult to remove.

For comparable selectivities for HMD, the catalysts which are doped with Ti make it possible to substantially restrict the content of DCH impurities: 0.028% (Example 2) against 0.044% (Comparative Test A) and 0.039% (Example 6) against 0.065% (Comparative Test B).

We claim:

1. A process for the hydrogenation of nitriles to amines, said process comprising:

a) doping a Raney nickel type catalyst with at least one additional metal element selected from Group IVb of the Periodic Classification of the Elements which is derived from a Ni/Al/doping element metallurgic precursor alloy and wherein the doping element/Ni ratio by weight is between 0.05 and 10%; and b) exposing said catalyst to a nitrile in a liquid reaction medium which dissolves the nitrile along with at least one inorganic base selected from the group consisting of LiOH, NaOH, KOH, RbOH, and CsOH and thereby hydrogenate said nitrile.

2. The process according to claim 1, wherein said nitrile has the formula (I):

$$NC-R-CN \quad (I)$$

wherein R represents a linear or branched alkylene or alkenylene group having from 1 to 12 carbon atoms or a substituted or unsubstituted arylene or aralkylene group.

3. The process according to claim 2, wherein R represents a linear or branched alkylene radical having from 2 to 6 carbon atoms in the nitrile of formula (I).

4. The process according to claim 2, wherein the nitrile is selected from the group consisting of adiponitrile, methylglutaronitrile, ethyl succinonitrile, malononitrile, succinonitrile, glutaronitrile and mixtures thereof.

5. The process according to claim 1, wherein the concentration of nitrile in the total reaction medium is between 0.001% and 30% by weight.

6. The process according to claim 5, wherein the concentrate of nitrile in the total reaction medium is between 0.1% and 20% by weight.

7. The process according to claim 1, wherein the liquid reaction medium comprises water.

8. The process according to claim 7, wherein the liquid reaction medium comprises water in an amount less than or equal to 20% by weight of the total liquid reaction medium 9. The process according to claim 8, wherein the water is present in an amount between 0.1 % and 15% by weight o the total liquid reaction medium.

10. The process according to claim 1, wherein the liquid reaction medium contains a targeted amine.

11. The process according to claim 10, wherein the targeted amine is introduced into the liquid reaction mediun in a proportion of 50 to 99% by weight with respect to th weight of the total liquid reaction medium.

12. The process according to claim 11, wherein th targeted amine is introduced into the liquid reaction mediun is a proportion of 60 to 99% by weight with respect to th weight of the total liquid reaction medium.

13. The process according to claim 1, wherein the liqui reaction medium contains an alcohol and/or an amide.

14. The process according to claim 13, wherein th alcohol is selected from the group consisting of methano ethanol, propanol, isopropanol, butanol, glycols, polyol: and mixture thereof.

15. The process according to claim 14, wherein the glyco is ethylene glycol or propylene glycol.

16. The process according to claim 14, wherein the amide is dimethylformamide or dimethylacetamide.

17. The process according to claim 1, wherein the base is present in an amount greater than or equal to 0.1 mole/kg of catalyst.

18. The process according to claim 17, wherein the base is present in an amount between 0.1 and 2.0 mole/kg of catalyst.

19. The process according to claim 18, wherein the base is present in an amount between 0.5 and 1.5 mole/kg of catalyst.

20. The process according to claim 13, wherein the base is present is an amount greater than or equal to 0.05 mole/kg of catalyst.

21. The process according to claim 20, wherein the base is present in an amount between 0.1 to 10.0 mole/kg of catalyst.

22. The process according to claim 21, wherein the base is present in an amount between 1.0 and 8.0 mole/kg of catalyst.

23. The process according to claim 1, wherein the hydrogenation is carried out at a temperature in the reaction medium of less than or equal to 150° C.

24. The process according to claim 23, wherein the hydrogenation is carried out at a temperature in the reaction medium of less than or equal to 120° C.

25. The process according to claim 24, wherein the hydrogenation is carried out at a temperature in the reaction medium of less than or equal to 100° C.

* * * * *